United States Patent [19]

Salzburg et al.

[11] Patent Number: 4,713,389
[45] Date of Patent: Dec. 15, 1987

[54] FUNGICIDALLY AND BACTERICIDALLY ACTIVE ACYLATED SACCHARIN DERIVATIVES

[75] Inventors: Herbert Salzburg; Manfred Hajek, both of Cologne; Hermann Hagemann, Leverkusen; Engelbert Kühle, Bergisch-Gladbach; Wolfgang Führer, Hennef; Gerd Hänssler, Leverkusen; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 774,271

[22] Filed: Sep. 10, 1985

[30] Foreign Application Priority Data

Sep. 12, 1984 [DE] Fed. Rep. of Germany ....... 3433391

[51] Int. Cl.[4] .................... A01N 47/38; C07D 275/06
[52] U.S. Cl. ...................................... 514/373; 548/210
[58] Field of Search ............... 548/209, 213, 210, 214; 514/373

[56] References Cited

U.S. PATENT DOCUMENTS 3,264,314  8/1966  Baker et al. ........................ 548/210

FOREIGN PATENT DOCUMENTS 1953422  5/1970  Fed. Rep. of Germany .
2507599  6/1982  France .
7329134  9/1973  Japan .................... 548/209
1278111  10/1969  United Kingdom .

OTHER PUBLICATIONS

Ariens, et al., *Drug Design*, Academic Press, New York, (1971), 44–45.
McOmie, J. F. W., *Protective Groups in Organic Chemistry*, Plenum Press, New York, (1973), pp. 46–49, 54, 55, 60, 61.
Japanese Patent Report, Pharmaceuticals Photographic, vol. R, No. 21, pp. 2 and 3, (Japanese Pat. No. 7014–301).

*Primary Examiner*—Mark L. Berch
*Assistant Examiner*—Diana G. Rivers
*Attorney, Agent, or Firm*—Sprung Horn Kramer & Woods

[57] ABSTRACT

Fungicidally and bactericidally active novel acylated saccharins of the formula

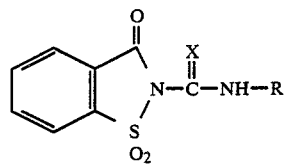

in which
X is oxygen or sulphur and
R is $-CO-R^1$ or $-SO_2-OR^2$,
$R^1$ is alkyl, halogenalkyl, alkoxy, halogenoalkoxy or alkylthio, or is optionally substituted aryl, aryloxy or arylthio, cycloalkoxy or $-NR^3R^4$,
$R^2$ is alkyl or phenyl,
$R^3$ is alkyl, and
$R^4$ is alkyl, phenyl, halogenoalkylthio, alkoxycarbonyl or phenoxycarbonyl, or
$-NR^3R^4$ is a saccharin radical.

12 Claims, No Drawings

FUNGICIDALLY AND BACTERICIDALLY ACTIVE ACYLATED SACCHARIN DERIVATIVES

The invention relates to new acylated saccharine derivatives, a process for their preparation and their use in agents for combating pests.

It is already known that alkylaminocarbonylsaccharin derivatives, for example N-[methylaminocarbonyl]saccharin, have a fungicidal activity (compare, for example, DE-OS (German Published Specification) No. 1,953,422). Halogenated phenylaminocarbonyl-saccharin derivatives, such as, for example, N-[3,4-dichlorophenylaminocarbonyl]saccharin and their bactericidal and fungicidal action are furthermore known (compare U.S. Pat. No. 3,264,314).

3-Alkenyloxy-isosaccharin derivatives and their fungicidal activity are furthermore known (compare Japanese Patent Application No. 70 14 301).

New acylated saccharin derivatives of the general formula (I)

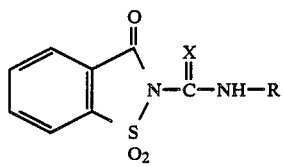

in which

X represents oxygen or sulphur and

R represents the grouping —CO—$R^1$ or —$SO_2$—$OR^2$, wherein $R^1$ represents alkyl, halogenoalkyl, alkoxy, halogenoalkoxy or alkylthio, or represents aryl, aryloxy or arylthio, each of which is optionally monosubstituted or polysubstituted by identical or different substituents, or furthermore represents cycloalkoxy or represents the group —$NR^3R^4$, $R^2$ represents alkyl or phenyl, $R^3$ represents alkyl and $R^4$ represents alkyl, phenyl, halogenoalkylthio, alkoxycarbonyl or phenoxycarbonyl, or $R^3$ and $R^4$, together with the nitrogen atom on which they stand, form a saccharin radical, have been found.

It has furthermore been found that the new acylated saccharin derivatives of the general formula (I)

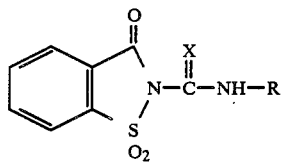

in which

X represents oxygen or sulphur and

R represents the grouping —CO—$R^1$ or —$SO_2$—$OR^2$, wherein $R^1$ represents alkyl, halongenoalkyl, alkoxy, halogenoalkoxy or alkylthio, or represents aryl, aryloxy or arylthio, each of which is optionally monosubstituted or polysubstituted by identical or different substituents, or furthermore represents cycloalkoxy or represents the group —$NR^3R^4$, $R^2$ represents alkyl or phenyl, $R^3$ represents alkyl and $R^4$ represents alkyl, phenyl, halogenoalkylthio, alkoxycarbonyl or phenoxycarbonyl, or $R^3$ and $R^4$, together with the nitrogen atom on which they stand, form a saccharin radical, are obtained by a process in which saccharin of the formula (II)

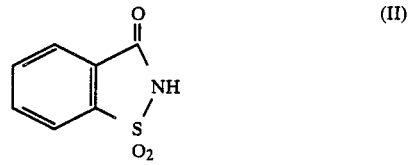

is reacted with iso- or thioiso-cyanate derivatives of the formula (III)

$$XCN—R \qquad (III)$$

in which

X and R have the abovementioned meaning, if appropriate in the presence of a solvent or diluent and if appropriate in the presence of a catalyst.

Finally, it has been found that the new acylated saccharin derivatives have a good action against pests, in particular against fungi and bacteria.

Surprisingly, the acylated saccharin derivatives of the formula (I) according to the invention exhibit a more powerful biological activity than the compounds of the same type of action which are already known from the prior art. The compounds according to the invention thus represent an enrichment of the art.

Formula (I) provides a general definition of the acylated saccharin derivatives according to the invention. Preferred compounds of the formula (I) are those in which X represents oxygen or sulphur and R represents the grouping —CO—R 1 or —$SO_2$—$OR^2$, wherein $R^1$ represents straight-chain or branched alkyl with 1 to 4 carbon atoms, or represents straight-chain or branched halogenoalkyl or halogenoalkoxy with in each case 1 to 6, in particular 1 to 4, carbon atoms and 1 to 5, in particular 1 to 3, identical or different halogen atoms, or represents straight-chain or branched alkoxy or alkylthio with in each case 1 to 10 carbon atoms, or represents aryl, aryloxy or arylthio with in each case 6 to 10 carbon atoms, each of which is optionally mono-, di-, tri-,tetra- or penta-substituted by identical or different substituents, substituents of the aryl which may be mentioned being: halogen, straight-chain or branched alkoxy with 1 to 4 carbon atoms, alkoxycarbonyl with 1 to 4 carbon atom in the alkoxy part, straight-chain or branched alkyl with 1 to 4 carbon atoms and N-halogenoalkyl-N-halogenoalkylthioamino with 1 to 3 carbon atoms and 1 to 5 identical or different halogen atoms per halogenoalkyl radical; or furthermore represents cycloalkoxy with 3 to 6 carbon atoms or represents the group —$NR^3R^4$, $R^2$ represents straight-chain or branched alkyl with 1 to 4 carbon atoms or phenyl, $R^3$ represents straight-chain or branched alkyl with 1 to 8 carbon atoms and $R^4$ represents straight-chain or branched alkyl with 1 to 4 carbon atoms, phenyl, halogenoalkylthio with 1 to 4 carbon atoms and 1 to 5 identical or different halogen atoms, alkoxycarbonyl with 1 to 4 carbon atoms in the alkoxy part or phenoxycarbonyl, or $R^3$ and $R^4$, together with the nitrogen atom on which they stand, form a saccharin radical.

Particularly preferred compounds of the formula (I) are those in which

X represents oxygen or sulphur and

R represents the grouping —CO—$R^1$ or —SO$_2$—$OR^2$, wherein $R^1$ represents methyl or ethyl, or represents straight-chain or branched halogenoalkyl or halogenoalkoxy with in each case 1 to 3 carbon atoms and 1 to 3 identical or different fluorine and chlorine atoms, or represents straight-chain or branched alkoxy with 1 to 10 carbon atoms, or represents straight-chain or branched alkylthio with 1 to 4 carbon atoms, or represents phenyl, phenoxy or phenylthio, each of which is optionally mono-, di- or tri-substituted by identical or different substituents from the group comprising chlorine, fluorine, methoxy, ethoxy, methyl, ethyl, methoxycarbonyl, ethoxycarbonyl and N-tri-fluoromethyl-N-fluorodichloromethylthioamino, or represents cyclohexoxy or represents the group —$NR^3R^4$, $R^2$ represents methyl, ethyl or phenyl, $R^3$ represents straight-chain or branched alkyl with 1 to 5 carbon atoms and $R^4$ represents methyl, ethyl, phenyl, phenoxycarbonyl, methoxycarbonyl, ethoxycarbonyl or halogenoalkylthio with 1 to 3 carbon atoms and 1 to 3 identical or different fluorine and chlorine atoms, or $R^3$ and $R^4$, with the nitrogen atom on which they stand, form a saccharin radical.

Especially preferred compounds of the formula (I) are those in which

X represents oxygen and

R represents the grouping —CO—$R^1$, wherein $R^1$ represents methoxy, ethoxy, n-propoxy, isopropoxy, n-butoxy, iso-butoxy, tert.-butoxy, pentoxy, hexoxy, 2-n-butyl-butoxy, chloromethoxy, 2,2,2-trifluoroethoxy, 1-chloromethyl-2-chloroethoxy, methylthio, ethylthio, n-propylthio, isopropylthio, phenoxy, phenylthio, cyclohexoxy, 2-methoxy-phenoxy, 4-methoxy-phenoxy, 2-chlorophenoxy, 4-chlorophenoxy, 2,4-dichlorophenoxy, 2-methoxycarbonyl-phenoxy, 2-chlorophenylthio, 4-chlorophenylthio, N-methyl-N-phenylamino, N-ethyl-N-phenylamino, N-n-propyl-N-phenyl-amino, N-n-butyl-N-phenyl-amino, N-n-butyl-N-trichloromethylthio-amino, N-methyl-N-phenoxycarbonylamino, N-ethyl-N-phenoxy-carbonyl-amino, N-n-propyl-N-phenoxy-carbonyl-amino, N-methyl-N-methoxy-carbonyl-amino, N-ethyl-N-ethoxy-carbonyl-amino, N-n-butyl-N-phenoxy-carbonyl-amino, N-iso-butyl-N-phenoxy-carbonyl-amino, N-iso-pentyl-N-phenoxy-carbonyl-amino, 2-[N-trifluoromethyl-N-dichloro-fluoromethyithio-amino]-phenyl, 3-[N-trifluoromethyl-N-dichlorofluoromethylthio-amino]-phenyl, 4-[N-trifluoromethyl-N-dichlorofluoro- methylthio-amino]-phenyl or 1,1-dioxide-3-keto2H,3H-1,2-benzisothiazolyl, or X represents oxygen, R represents the grouping —$SO_2$—$OR^2$, wherein $R^2$ represents phenyl, methyl or ethyl.

If, for example, saccharin and methoxycarbonyl isocyanate or dimethylaminocarbonyl isocyanate are used as starting materials, the courses of the reactions can be represented by the following equations:

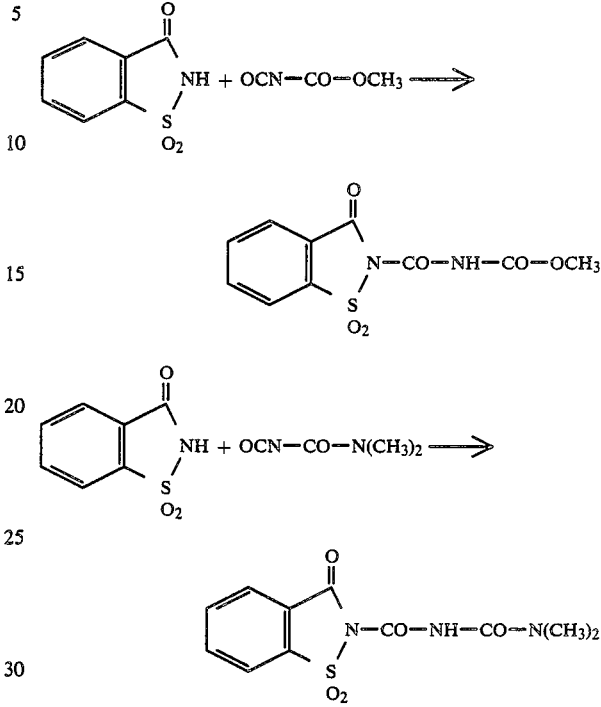

The saccharin of the formula (II) required as a starting substance for carrying out the process according to the invention is known and is also commercially available on an industrial scale.

The iso- or thioiso-cyanate derivatives of the formula (III) furthermore required as starting substances are likewise known, and can be prepared by processes which are known from the literature. General instructions are reported in standard works, such as Houben-Weyl "Methoden der Organischen Chemie" ("Methods of Organic Chemistry") E 4, 1983, Thieme-Verlag Stuttgart, and compounds in which R represents, for example, alkylcarbonyl can be prepared as described in "J. Org. Chem." 27, 3742 et seq. (1962) and 28, 1805 et seq. (1962), and also "Angewandte Chemie" 89, 789 (1977). Compounds in which R represents, for example, alkoxycarbonyl can be prepared as described in "Berichte der Deutschen Chem. Ges." 39, 688 et seq. (1906).

Possible diluents for the process are all inert organic solvents. These include, preferably, aliphatic or aromatic, optionally halogenated hydrocarbons, such as, for example, benzine, benzene, toluene, xylene, petroleum ether, pentane, hexane, cyclohexane, methylene chloride, chloroform, carbon tetrachloride or chlorobenzene; ethers, such as diethyl ether, diisopropyl ether, ethylene glycol dimethyl ether, dioxane or tetrahydrofuran; ketones, such as acetone or butanone; nitriles, such as acetonitrile or propionitrile; and esters of carboxylic acids, such as ethyl acetate, butyl acetate or ethyl propionate.

The process according to the invention can also be carried out in the absence of a diluent or solvent. In this case, the acylating component is preferably employed in an excess of 0.1 to 5 equivalents. When the reaction has ended, the excess reagent is distilled off in vacuo.

The reaction temperatures can be varied within a substantial range in carrying out the process according to the invention. In general, the reaction is carried out between 0° C. and 100° C., preferably between 25° C. and 60° C.

The process according to the invention is preferably carried out under normal presure.

Catalysts which are employed are the catalysts customary for isocyanate additions, such as, for example, dibutyltin dilaurate, triethylamine and triethylenediamine (DABCO).

In one variant of the reaction, an alkoxycarbonylaminocarbonyl halide, preferably a cholride, can be employed instead of the alkoxycarbonyl isocyanates. In this case also, approximately one equivalent of an auxiliary base, such as triethylamine or pyridine, sodium bicarbonate or sodium carbonate, is advantageously added.

The active compounds according to the invention exhibit a powerful microbicidal action and can be employed in practice for combating undesired microorganisms. The active compounds are suitable for use as plant protection agents.

Thus, for example, fungicidal agents are employed in plant protection for combating Plasmodiophoromycetes, Oomycetes, Chytridiomycetes, Zygomycetes, Ascomycetes, Basidigomycetes and Deuteromycetes.

Bactericidal agents are used, for example, in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Botrytis species, such as, for example, *Botrytis cinerea;* Plasmopara species, such as, for example, *Plasmopara viticola;* Uromyces species, such as, for example, *Uromyces appendiculatus;* Sphaerotheca species, such as, for example, *Sphaerotheca fuliginea;* Venturia species, such as, for example, *Venturia inaeqalis;* Podosphaera species, such as, for examle, *Podosphaera Leucotricha;* Phytophthora species, such as, for example, *Phytophthora infestans;* Erysiphe species, such as, for example, *Erysiphe graminis;* Puccinia species, such as, for example, *Puccinia recondita;* Fusarium species, such as, for example, *Fusarium culmorum;* Ustilago species, such as, for example, *Ustilago nuda* or *Ustilago avenae;* Septoria species, such as, for example, *Septoria nodorum;* Tilletia species, such as, for example, *Tilletia caries;* Xanthomonas species, such as, for example, *Xanthomonas oryzae;* Pseudomonas species, such as, for example *Pseudomonas lachrymans;* Pyricularia species, such as, for example, *Pyricularia oryzae;* Pellicularia species, such as, for example, *Pellicularia sasakii;* Erwinia species, such as, for example *Erwinia amylovova;* Pyrenophora species, such as, for example, Pyrenophora teres (conidia form: Drechslera, syn: Heliminthosporium); Leptosphaeria species, such as, for example, *Leptosphaeria nodorum;* Cochliobolus species, such as, for example, *Cochliobolus sativus* (conidia form: Drechslera, syn: Helminthosporium) and Cercospora species, such as, for example, *Cercospora canescens.*

The good toleration, by plants, of the active compounds, at the concentrations required for combating plant diseases, permits treatment of above-ground parts or plants, of vegetative propagation stock and seeds and of the soil.

As agents for combating pests, the active compounds according to the invention can be employed with particularly good success for combating fruit and vegetable diseases, such as, forexample, against the brown rot causative orgaism (*Phytophthora infestens*) on tomatoes, and also for combating cereal diseases, for example caused by *Pyrenophora teres, Septoria nodorum, Fusarium culmorum* and *drechslera graminea,* and furthermore for combating rice dieases, such as, for example, the leaf spot disease causative orgaism ( *Pyricularia oryzae*). The compounds also have a bactericidal action.

The active compounds can be converted to the customary formulations, such as solution, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or a alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of imorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanim oxide and Prussian Blue, and organic dyestuffs, such as alizarin dyestuffs, azo dyestuffs and metal phthalocyanine dyestuffs, and trace nutrients such as salts or iron, manganese, boron, copper, cobalt, molybdenum and zinc.

The formulations in general contain between 0.1 and 95 percent by weight of active compound, preferably between 0.5 and 90%.

The acive compounds according to the invention can be present in the formulations as a mixture with other known active compounds, such as fungicides, insecticides, acaricides and herbicides, and in mixtures with of fertilizer and growth regulators.

The active compounds can be used as such or in the form of their formulations or the use forms prepared therefrom, such as ready-to-use solutions, emulsifiable concentrates, emulsion, foams, suspensions, wettable powders, pastes, soluble powders, dusts and granules. They are ued in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations 0.00001 to 0.01% by weight, preferably 0.0001 to 0.02% by weight, are required at the place of action.

PREPARATION EXAMPLES

EXAMPLE 1

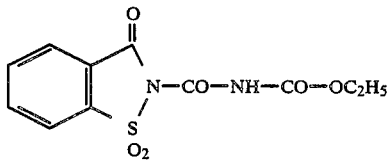

0.2 ml of triethylamine is added to 17.3 g (0.095 mole) of saccharin in 250 ml of acetone, and 11.5 g (0.1 mole) of ethoxycarbonyl isocyanate are then added dropwise. After the mixture has been stirred at 45° C. for 1 hour, the reaction has ended. Concentration in vacuo gives 28.2 g (99% of theory) of N-ethoxycarbonylaminocarbonyl)-saccharin of melting point 148° C.

EXAMPLE 2

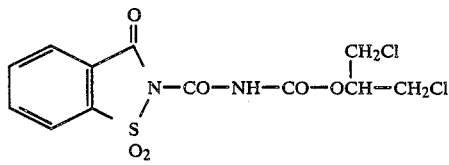

36.0 g (99% of theory) of N-(1,3-dichloroisopropyl-2-oxycarbonylaminocarbonyl)-saccharin of melting point 208° C. are obtained analogously to Example 1 from 17.3 g of saccharin and 19.7 g (0.1 moles of 1,3-dichloroisoropyl-2-oxycarbonyl isocyanate in 200 ml of methylene chloride.

EXAMPLE 3

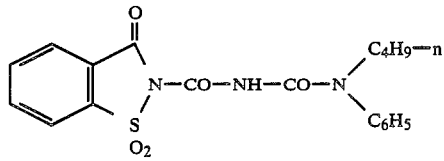

9.2 g of saccharin (0.05 mole) are dissolved in 100 ml of dioxane with 0.1 g of triethylenediamine (DABCO), and 10.9 g (0.05 mole) of butylphenylaminocarbonyl iscyanate are then added. The mixture is boiled under reflux for 6 hours, with exclusion of moisture, and is then concentrated and the residue is stirred three times with diisopropyl ether. 6 g (30% of theory) of n-butylphenylaminocarbonylaminocarbonyl-saccharin of melting point 210° C. are obtained.

The following compounds of the formula (I) are prepared in a corresponding manner according to the general preparation data:

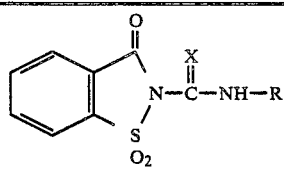

| Example No. | X | R | Physical constants [melting point: °C.] |
|---|---|---|---|
| 4 | O | $-CO-OCH_2-CH(CH_3)_2$ | 146 |
| 5 | O | $-CO-OCH_2-CF_3$ | 181 |
| 6 | O | $-CO-SC_3H_7-n$ | 179 |
| 7 | O | $-CO-OCH_2-\underset{(CH_2)_3-CH_3}{CH}-CH_2-CH_3$ | oil |
| 8 | O | $-CO-O-\phenyl$ | 112 |
| 9 | S | $-CO-OC_2H_5$ | 243 |
| 10 | O | $-CO-S-\phenyl$ | 180 |
| 11 | O | $-CO-OCH_2Cl$ | 167 |
| 12 | O | $-CO-OC_6H_{11}$ | 118 |
| 13 | O | $-CO-O-\phenyl-OCH_3$ | oil |
| 14 | O | $-CO-OC_4H_9-n$ | 224 |
| 15 | O | $-CO-N(SCCl_3)(C_4H_9-n)$ | oil |

-continued

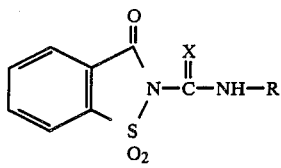

(I)

| Example No. | X | R | Physical constants [melting point: °C.] |
|---|---|---|---|
| 16 | O | 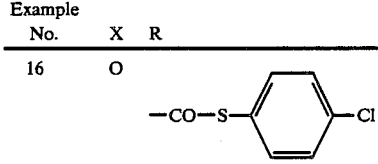 —CO—S—⟨ ⟩—Cl | oil |
| 17 | O | 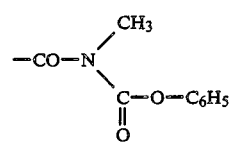 —CO—N(CH₃)—C(=O)—O—C₆H₅ | 190 |
| 18 | O | 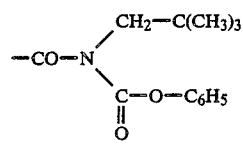 —CO—N(CH₂—C(CH₃)₃)—C(=O)—O—C₆H₅ | oil |
| 19 | O | 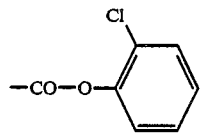 —CO—O—⟨ ⟩—Cl | 194 |
| 20 | O | 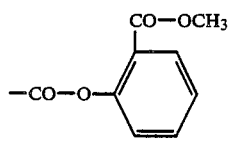 —CO—O—⟨ ⟩—CO—OCH₃ | 175 |
| 21 | O | 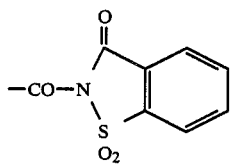 | 265 |
| 22 | S | —CO—OC₆H₅ | 210 |
| 23 | O | —SO₂—O—C₆H₅ | 161 |
| 24 | O | 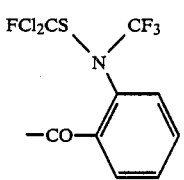 FCl₂CS, CF₃ N—⟨ ⟩—CO— | 98 |
| 25 | O | 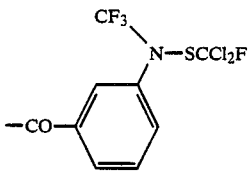 CF₃, N—SCCl₂F —CO—⟨ ⟩ | 198 |
| 26 | O | 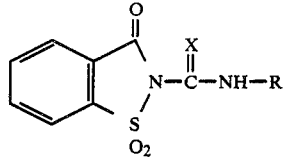 —CO—⟨ ⟩—N(CF₃)(SCCl₂F) | oil |

USE EXAMPLES

The compounds shown below are employed as comparison stances in the use examples which follow:

$$\begin{array}{c} CH_2-NH-CS-S \\ | \quad\quad\quad\quad\quad\quad Zn \\ CH_2-NH-CS-S \end{array}$$ (A)

Zinethylene-1,2-bis-dithiocarbamate (B) 3-Allyloxy-1,2-benzisothiazole-1,1-dioxide $$(CH_3)_2N-SO_2-N(C_6H_5)-SCCl_2F$$ (C)

N,N-Dimethyl-N'-phenyl-N'-dichlorofluoro-methylthio-sulphamide

EXAMPLE A

Pyricularia test(rice)/protective Solvent: 12.5 parts by weight of acetone Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to preparation Examples 2, 14, 8, 5, 23, 10, 1, 13, 16, 15 and 24.

EXAMPLE B

Pyricularia test (rice)/systemic Solvent: 12.5 parts by weight of acetone Emlsifier: 0.3 parts by weight of alkylaryl polyglycol ether To produce a suitable preparation of active compound, 1 part by weight of active compound is mixed with the sated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to preparation Examples 2, 14, 8, 5, 4, 23, 10, 11, 13, 16,15 and 26. 11, 13, 16, 15 and 26.

EXAMPLE C

Phytophthora test (tomato)/protective Solvent: 4.7 parts by weight of acetone Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compounds according to preparation Examples 25 and 24.

EXAMPLE D

*Pyrenophora teres* test (barley)/protective Solvent: 100 parts by weight of dimethylformamide Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of *Pyrenophora teres*. The plants then remain in an incubation cabinet at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to preparation Example 24.

It will be understood that the specification and examples are illustrative but not limitative of the present invention and that other embodiments within the spirit and scope of the invention will suggest themselves to those skilled in the art.

We claim:

1. An acylated saccharin of the formula

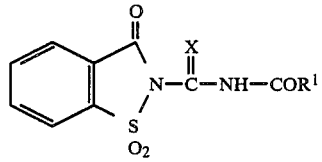

in which
X is oxygen or sulphur,
$R^1$ is carbon atoms, halogenoalkyl or halogenoalkoxy with in each case 1 to 6 carbon atoms and 1 to 5 halogen atoms, alkoxy or alkylthio with in each case 1 to 10 carbon atoms, or unsubstituted aryl, aryloxy or arylthio with in each case 6 or 10 carbon atoms, or aryl, aryloxy or arylthio with in each case 6 or 10 carbon atoms each of which is mono-, di-, tri, tetra- or penta-substituted by halogen, alkoxy with 1 to 4 carbon atoms, alkoxycarbonyl with 1 to 4 carbon atoms and/or N-halogenoalkyl-N-halogenoalkylthioamine with 1 to 3 carbon atoms and 1 to 5 halogen atoms per halogenoalkyl radical; or is cycloalkoxy with 3 to 6 carbon atoms or $-NR^3R^4$,
$R^3$ is alkyl with 1 to 8 carbon atoms, and
$R^4$ is alkyl with 1 to 4 carbon atoms, phenyl, halogenoalkylthio with 1 to 4 carbon atoms and 1 to 5 halogen atoms, alkoxycarbonyl with 1 to 4 carbon atoms in the alkoxy part or phenoxycarbonyl, or $-NR^3R^4$ is a saccharin radical.

2. An acylated saccharin according to claim 1, in which
$R^1$ is methyl or ethyl, or halogenoalkyl or halogenoalkoxy with in each case 1 to 3 carbon atoms and 1 to 3 fluorine plus chlorine atoms, or alkoxy with 1 to 10 carbon atoms, or alkylthio with 1 to 4 carbon atoms, or unsubstituted phenyl, phenoxy or phenylthio or phenyl, phenoxy or phenylthio each of which is mono-, di- or tri-substituted by chlorine, fluorine, methoxy, ethoxy, methyl, ethyl, methoxycarbonyl, ethoxycarbonyl and/or N-trifluoromethyl-N-fluorodichloromethylthioamino, or is cyclohexoxy or $-NR^3R^4$,
$R^3$ is alkyl with 1 to 5 carbon atoms, and
$R^4$ is methyl, ethyl, phenyl, phenoxycarbonyl, methoxycarbonyl, ethoxycarbonyl or halogenoalkylthio with 1 to 3 carbon atoms and 1 to 3 fluorine plus chlorine atoms, or $-NR^3R^4$ is a saccharin radical.

3. An acylated saccharin according to claim 1, in which
X is oxygen, and
$R^1$ is methoxy, ethoxy, n-propoxy, isopropoxy, n-butoxy, iso-butoxy, tert.--butoxy, pentoxy, hexoxy, 2-n-butyl-butoxy, chloromethoxy, 2,2,2-trifluoroethoxy, 1-chloromethyl-2-chloroethoxy, methylthio, ethylthio, n-propylthio, isopropylthio, phenoxy, phenylthio, cyclohexoxy, 2-methoxy-phenoxy, 4-methoxy-phenoxy, 2-chlorophenoxy, 4-chloro-phenoxy, 2,4-dichlorophenoxy, 2-methoxycarbonyl-phenoxy, 2-chlorophenylthio, 4-chlorophenylthio, N-methyl-N-phenylamino, N-ethyl-N-phenylamino, N-n-propyl-N-phenyl-amino, N-n-butyl-N-phenyl-amino, N-n-butyl-N-trichloro-methylthio-amino, N-methyl-N-phenoxycarbonylamino, N-ethyl-N-phenoxy-carbonyl-amino, N-n-propyl-N-phenoxy-carbonyl-amino, N-methyl-N-methoxy-carbonyl-amino, N-ethyl-N-ethoxy-carbon-yl-amino, N-n-butyl-N-phenoxy-carbonyl-amino, N-iso-butyl-N-phenoxy-carbonyl-amino, N-iso-pentyl-N-phenoxy-carbonyl-amino, 2-[N-trifluoromethyl-N-dichloro-fluoromethylthio-amino]-phenyl, 3-[N-trifluoromethyl-N-dichlorofluoromethylthio-amino]-phenyl, 4-[N-trifluoromethyl-N-dichlorofluoro-methylthio-amino]-phenyl or 1,1-dioxide-3-keto-2H,3H-1,2-benzisothiazolyl.

4. An acylated saccharin according to claim 1, in which

X is oxygen and.

5. An acylated saccharin according to claim 1, wherein such compound is N-(1,3-dichloroisopropyl-2-oxycarbonyl-aminocarbonyl)-saccharin of the formula

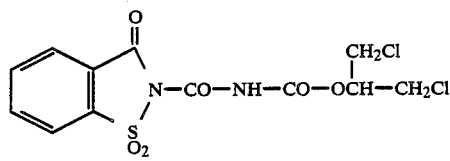

6. An acylated saccharin according to claim 1, wherein such compound is N-(n-butyl-phenylaminocarbonylaminocarbonyl-)-saccharin of the formula

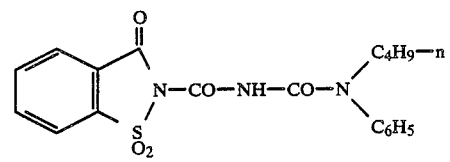

7. An acylated saccharin according to claim 1, wherein such compound is N-(phenoxycarbonylaminocarbonyl)-saccharin of the formula

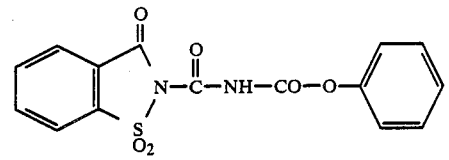

8. An acylated saccharin according to claim 1, wherein such compound is N-(n-butoxycarbonylaminocarbonyl)-saccharin of the formula

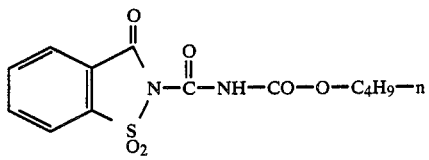

9. An acylated saccharin according to claim 1, wherein such compound is N-[2-(N-trifluoromethyl-N-dichloro fluoromethylthioamino)-phenyl carbonylaminocarbonyl)saccharin of the formula

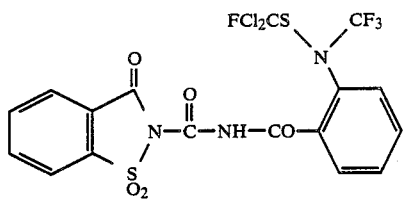

10. A fungicidal and bactericidal composition comprising a fungicidally and bactericidally effective amount of an acylated saccharin according to claim 1 in admixture with a diluent.

11. A method of combating fungi and bacteria which comprises applying thereto or to a habitat thereof a fungicidally or bactericidally effective amount of an acylated saccharin according to claim 1.

12. The method according to claim 11, wherein the acylated saccharin is

N-(1,3-dichloroisopropyl-2-oxycarbonyl-aminocarbonyl)-saccharin,

N-(n-butyl-phenylaminocarbonylamino carbonyl)-saccharin,

N-(phenoxycarbonylaminocarbonyl)-saccharin,

N-(n-butoxycarbonylaminocarbonyl)-saccharin or

N-[2-(N-trifluoromethyl-N-dichloro-fluoromethylthioamino)-phenyl carbonyl-aminocarbonyl)-saccharin.

* * * * *

UNITED STATES PATENT AND TRADEMARK OFFICE
CERTIFICATE OF CORRECTION

PATENT NO. : 4,713,389

DATED : Dec. 15, 1987

INVENTOR(S) : Salzburg et al.

Page 1 of 2

It is certified that error appears in the above-identified patent and that said Letters Patent is hereby corrected as shown below:

| | |
|---|---|
| Col. 1, line 65 | Correct spelling of --halogenoalkyl-- |
| Col. 2, line 58 | Delete "atom" and substitute --atoms-- |
| Col. 5, line 27 | Correct spelling of --Basidiomycetes-- |
| Col. 6, line 4 | Delete "forexample" and insert --for example-- |
| Col. 6, line 5 | Correct spelling of --organism-- |
| Col. 6, line 10 | Correct spelling of --organism-- |
| Col. 6, line 26 | Delete "a" |
| Col. 6, line 48 | Correct spelling of --inorganic-- |
| Col. 7, line 7 | Correct spelling of --active-- |
| Col. 7, line 10 | Delete "of" |
| Col. 7, line 17 | Correct spelling of --used-- |
| Col. 7, line 68 | Delete "moles" and insert --mole)-- |
| Col. 7, line 68 | Correct spelling of --dichloroisopropyl-- |
| Col. 8, line 16 | Correct spelling of --isocyanate-- |
| Col. 11, line 10 | Correct spelling of --stated-- |
| Col. 11, line 26 | Delete "11, 13, 16, 15 and 26" in the second instance |

UNITED STATES PATENT AND TRADEMARK OFFICE
CERTIFICATE OF CORRECTION

PATENT NO. : 4,713,389

DATED : Dec. 15, 1987

INVENTOR(S) : Salzburg et al

It is certified that error appears in the above-identified patent and that said Letters Patent is hereby corrected as shown below:

Col. 12, line 22　　　　Insert --alkyl with 1 to 4-- after "R'"

Signed and Sealed this

Twelfth Day of July, 1988

Attest:

DONALD J. QUIGG

Attesting Officer　　　Commissioner of Patents and Trademarks